United States Patent [19]

Vlock

[11] Patent Number: 4,978,297
[45] Date of Patent: Dec. 18, 1990

[54] HANDPIECE WITH ADDITIVE CHAMBER

[76] Inventor: David G. Vlock, 12 Fifth Ave., New York, N.Y. 10011-8857

[21] Appl. No.: 409,240

[22] Filed: Sep. 19, 1989

[51] Int. Cl.⁵ ............................................. A61C 3/02
[52] U.S. Cl. ...................................... 433/88; 433/126
[58] Field of Search ...................... 433/88, 84, 85, 87, 433/114, 125, 126

[56] References Cited

U.S. PATENT DOCUMENTS

| | | | |
|---|---|---|---|
| 2,400,912 | 5/1946 | Britt et al. | 433/82 |
| 2,814,877 | 12/1957 | Tilden | 433/88 |
| 4,060,870 | 12/1977 | Cannarella | 433/80 |
| 4,315,741 | 2/1982 | Reichl | 433/82 |
| 4,608,018 | 8/1986 | Ghedini et al. | 433/88 |

FOREIGN PATENT DOCUMENTS

| | | | |
|---|---|---|---|
| 1291439 | 3/1969 | Fed. Rep. of Germany | 433/82 |
| 2624721 | 6/1989 | France | 433/88 |

Primary Examiner—John J. Wilson
Attorney, Agent, or Firm—Notaro & Michalos

[57] ABSTRACT

A dental handpiece device comprises a housing handle with a water supply line which extends through the interior of the handle or along the outside of the handle. An auxiliary chamber is formed in or is connected to the handle housing. The auxiliary chamber communicates with the water supply line and may receive an additive in tablet form. The additive slowly dissolves as water passes through the auxiliary chamber. The water supply line terminates at a nozzle for spraying water near the head end of the handle housing which carries a rotating tool such as a bur or a brush. The additive is advantageously a disinfectant for disinfecting the operative area and the mist and aerosol generated by the handpiece.

8 Claims, 2 Drawing Sheets

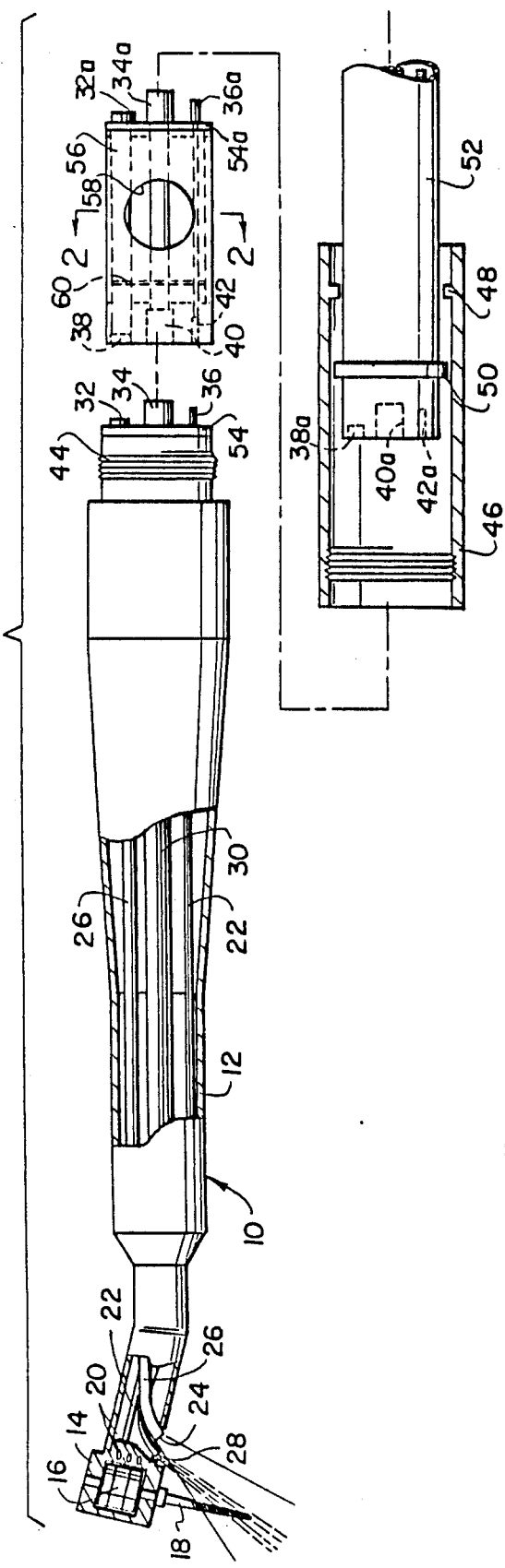
FIG. I
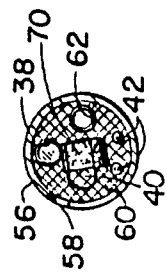
FIG. 2
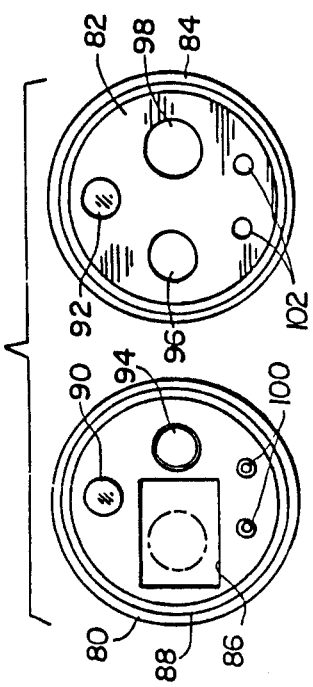
FIG. 3

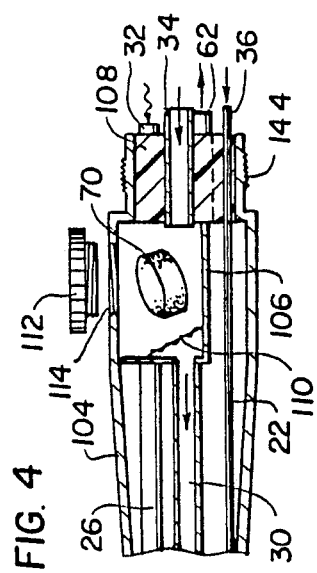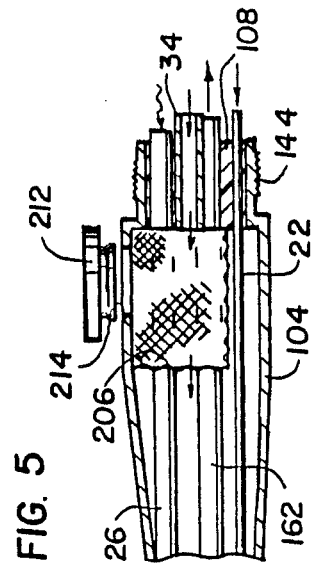

HANDPIECE WITH ADDITIVE CHAMBER

FIELD AND BACKGROUND OF THE INVENTION

The present invention relates in general to handpieces used in dentistry, and in particular to a new and useful handpiece having a chamber for receiving an additive that is dissolved into a stream of water passing along the handpiece.

Dental handpieces have an exceedingly wide application in the practice of dentistry. Handpieces include an elongated housing which is used as a handle by the dental practitioner. A rotor is connected to one end of the housing for receiving a bur, brush, diamond stone, abrasive instrument or other rotary implement for cleaning and drilling dental surfaces. Various handpiece designs include rotors which rotate on the axis of the elongated housing or at a variety of angles to the axis of the elongated housing. Rotors are driven either mechanically by a motor connected to a shaft extending through the housing, or by fluid such as air which spins a turbine formed as part of the rotor.

A supply of water is often provided in a conduit extending through the housing or along the exterior of the housing. The conduit terminates at a nozzle near the rotary implement for irrigation during the dental procedure. Optical fiber bundles are also often provided through the housing. For illumination, the fiber bundle terminates at a light emitting end near the bur or brush. When a pneumatically driven turbine is used to spin the rotor, one or more air lines are provided through the housing which open at jet orifices directed against the turbine. It is conventional to provide an air return opening in the turbine chamber which communicates with the interior of the housing for returning air along the length of the housing. The handpiece housing generally includes a supply end which is remote from the rotor and which is detachably connected to hoses or conduits for supplying air, water, light, electricity or mechanical rotary power, depending on the design of the housing.

One example of a modern dental handpiece can be found in U.S. Pat. No. 4,146,964.

Some modern handpiece designs include swivel connections at the supply end of the housing which permit 360° rotation of the housing with respect to its supply hose.

During a dental procedure, large volumes of mist and aerosol are created by the handpiece. The water spray from the handpiece is agitated by the spinning instrument and is intermixed with suspended body fluids from the patient's mouth which may include saliva and blood. These mists and aerosols represent a potential health hazard since they may carry contagions both to the patient's mouth through the water supply, and from the patient's mouth back into the ambient air as a contaminated aerosol of water, saliva and blood.

No mechanism or technique is currently known for controlling this potentially dangerous source of infection.

SUMMARY OF THE INVENTION

The present invention is directed to a device and method of introducing an additive into the flow of water passing along or through a dental handpiece. This is done without disturbing the functionality of the handpiece or the fact that the handpiece can be readily connected to and removed from its sources of water, air, mechanical energy and light.

According to the present invention, the handpiece is provided with an auxiliary chamber which communicates with the water stream. Means are provided for introducing a tablet into the auxiliary chamber.

The tablet may advantageously include flavorants, antibiotics, sterilizing agents, mouth wash or various medications.

Alternatively, additives in powdered, paste or liquid form may be added to the auxiliary chamber.

According to the present invention, a tablet of sterilizing agent or disinfectant is added to the auxiliary chamber for each dental procedure. Subsequent to the dental procedure, the handpiece along with its auxiliary chamber are sterilized for subsequent reuse. The addition of disinfectant to the water stream protects the patient against any contagion which may find its way into the water stream and helps disinfect the patient's mouth during the dental procedure. The introduction of disinfectant into the water stream also disinfects the mist and aerosols emitted from the patient's mouth and thus protects the dental practitioner and assisting staff from potentially harmful airborne contaminants.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which the preferred embodiments of the invention are illustrated.

BRIEF DESCRIPTION OF THE DRAWINGS

In the drawings:

FIG. 1 is an exploded view of a typical dental handpiece which includes an auxiliary chamber for an additive according to the present invention;

FIG. 2 is a sectional view taken along line 2—2 of FIG. 1 and showing the auxiliary chamber;

FIG. 3 is an exploded view showing the mating ends of a handpiece and coupling arrangement therefor, including a further embodiment of the invention;

FIG. 4 is a fragmentary sectional view of a dental handpiece housing incorporating an auxiliary chamber according to the present invention; and FIG. 5 is a view similar to FIG. 1 showing a further embodiment of the invention.

DESCRIPTION OF THE PREFERRED EMBODIMENTS

Referring to the drawings in particular, the invention embodied in FIGS. 1 and 2 comprises a dental handpiece generally designated 10 having a housing 12 with a head 14 at one end. Head 14 defines a turbine chamber which contains a rotatably mounted turbine 16.

A bur or diamond stone 18 is detachably connected to the turbine for rotation at high speed with the turbine.

A plurality of air jet orifices 20 are directed into the turbine chamber tangentially at an angle against the turbine 16 for spinning the turbine in head 14. One or more air supply lines 22 are connected to the orifices 20 and extend through the interior of the housing 12.

Modern handpieces also include illumination means in the form of an optical fiber bundle 26 which terminates at a light emitting end 24 near the handpiece head 14. The working area is thus illuminated during the dental procedure.

A nozzle 28 is also provided near the handpiece head 14 for spraying water toward the working area. Nozzle 28 is supplied by a water supply line 30 which also extends through the interior of the housing 12. In other handpiece models, the water supply line and nozzle are mounted outside the housing. The present invention seeks to improve that type of handpiece as well.

Although the rotation axis of turbine 16 is shown to be at an angle to the longitudinal axis of housing 12 in the embodiment of FIG. 1, handpieces are also known which spin a tool on an axis which extends parallel to the housing axis. In these handpieces, rotation is generally through a mechanical shaft or coupling extending along the axis of the housing and terminating at a gear which is engaged by the gear of a motor carried on the opposite end of the housing. While this type of known handpiece is not shown, it too can be improved by the present invention.

In the handpiece shown in FIG. 1, light, air and water are supplied through lines in a hose 52 which can be coupled and sealed to the supply end of housing 12. The supply end of housing 12 carries a threaded housing coupling 44 which threadably receives a sleeve 46 that is slideable on the hose 52 but trapped thereon by a sleeve flange 48 which engages against a hose flange 50 for pressing a coupling end of the hose against a coupling end of the handpiece.

In a typical conventional handpiece, the supply end of the housing includes a male fiber bundle coupling member 32 which can seat within a female coupling socket 38a in the end of the hose 52. A male water supply coupling member 34 can similarly seat within a female water supply coupling 40a. One or more air supply lines include male air line coupling members 36 can seat within female air line coupling sockets 42a. A rubber seal 54 surrounds the male coupling members and forms a positive seal with the female coupling members. This coupling is firmly established by flanges 48 and 50 which press the coupling members against each other when the sleeve 46 is threaded on to the housing coupling 44.

According to the present invention, an auxiliary chamber 56 having an opening 58 through its side, is interposed between the supply end of the handpiece housing 12 and the coupling end of the hose 52. The opening 58 is large enough to receive a tablet 70 which contains the desired additive or combination of additives. Male coupling member for light, water and air, shown at 32, 34 and 36 respectively, are reproduced at 32a, 34a, and 36a at one end of auxiliary chamber 56. An additional rubber seal 54a is also provided at this end for establishing sealed connections with socket members 38a, 40a and 42a at the end of the hose 52.

The opposite end of housing 56 includes socket members 38, 40 and 42 which are substantially identical to the socket members at the end of hose 52.

The water supply male coupling member 34a opens into the interior of chamber 56. The interior chamber 56 communicates with the socket member 40. In this way, the tablet can be introduced into the water stream being supplied to the hand piece. The hose visible in hole 58 in FIG. 1 represents an air return line shown at 62 in FIG. 2 which communicates with the interior of hand piece housing 12 for returning air from the handpiece head 14.

To avoid any blockage in the water coupling and socket members 34 and 40, a screen 60 is provided across the downstream end of housing 56.

The only mechanical modification required to the conventional handpiece shown in FIG. 1, is the lengthening of sleeve 46 so that it engages over and embraces the housing 56. In this embodiment of the invention, the interior surface of sleeve 46 may be provided with sealing material such as TEFLON (a trademark) or other sealing material for hermetically sealing the opening 58. Alternatively, if the inner surface of sleeve 46 and the outer surface of housing 56 are machined to cause tolerances, a good water seal can also be produced.

In those handpieces which have an external water supply conduit, an exterior auxiliary chamber is provided for plugging between the exterior water supply line and the water supply line connected to the housing for attachment to the nozzle 28.

FIG. 3 shows an alternate embodiment of the invention where the supply end of the handpiece is shown at the left and the coupling end of the supply hose is shown at the right. Mating male and female optical bundle members 90 and 92 are provided as well as male and female air supply couplings 100 and 102, and male and female air return coupling members 94 and 96.

A water supply opening 98 is also provided in the coupling face of the hose. The coupling face is covered by a rubber seal 82 which is firmly pressed against the coupling face at the end of the handpiece housing.

The coupling face of the handpiece housing also includes a large slot 86 which extends into an auxiliary chamber integrally formed at the supply end of the handpiece housing 80. The handpiece housing 80 has a threaded coupling 88 which threadably receives a sleeve 84. Sleeve 84 is analogous to sleeve 46 in the embodiment of FIG. 1.

The embodiment of FIG. 3 requires modification to a conventional handpiece for incorporating the integrally formed auxiliary chamber. Only the supply end of the handpiece need be modified, however, since a conventional hose coupling sleeve arrangement can be used.

FIG. 4 shows a further embodiment of the invention where the rear supply end of the handpiece housing 104 is provided with an auxiliary chamber 106 formed in the volume of the housing. A tablet receiving opening 114 is provided through the wall of the handpiece housing 104 and is threaded for receiving a threaded cap 112. Threaded cap 112 may include seals such as o-rings or the like for hermetically sealing opening 114. Tablet 70 is shown in chamber 106. Water is supplied through male coupling 34 which opens into chamber 106. A screen 110 avoids the introduction of undissolved tablet particles into the water supply line 30. As with the embodiment of FIG. 1, an optical bundle 26 extends through the housing and is positioned on one side of the chamber 104. This is supplied with light through male coupling 32. Air return coupling 62 communicates with the interior of chamber 104 for returning air which was originally supplied through the air couplings 36 and air supply lines 22. The coupling members are all embedding within a sealing plug 108 at the threaded housing coupling 144 of the housing 104.

FIG. 5 shows a further embodiment of the invention wherein part of the interior handpiece housing 104 forms an auxiliary chamber which is bounded by a cage 206 made of screen material. A tablet is introduced through opening 214 in housing 104 which can be sealed by a plug 212. Water emitted through coupling 34 enters into the housing 104 and passes through the cage 206 for slowly dissolving the tablet and introducing its material into the water stream. A nozzle at the active end of the housing (not shown in FIG. 5) is formed by simply boring a small hole through the housing.

Since the volume of the housing is used for water in the embodiment of FIG. 5, a separate air return line 162 must be provided for discharging the air which was initially supplied by air supply lines 22. As with the embodiment of FIG. 4, optical bundle 26 is positioned to one side of the cage 206. The sealing plug 108 and housing coupling 144 are the same as that used in the embodiment of FIG. 4.

While the specific embodiments of the invention have been shown and described in detail to illustrate the application of the principles of the invention, it will be understood that the invention may be embodied otherwise without departing from such principles.

What is claimed is:

1. A handpiece device for use with a water stream and an additive comprising:
   a handle housing having a head end;
   a tool receiving rotor rotatably mounted to said head end for receiving a rotary tool to be used in a procedure;
   water supply means operatively connected to said handle housing for defining a water stream terminating at a water nozzle adjacent said head end;
   auxiliary chamber means connected to said handle housing and defining an auxiliary chamber communicating with said water stream, said auxiliary chamber including an opening for receiving an additive for introduction of the additive into the water stream; and
   closure means connected to said auxiliary chamber means for opening said auxiliary chamber opening to receive the additive and for closing the auxiliary chamber opening for sealing the auxiliary chamber against loss of water from said water stream;
   said handle housing including a supply end opposite from said head end, said water supply means including a first water coupling connected to said supply end and a water supply hose having a second water supply coupling, said auxiliary chamber means comprising an auxiliary chamber member containing said auxiliary chamber therein, detachably connected to said handle housing, said auxiliary chamber member having a third water supply coupling for coupling to said first water supply coupling and a fourth water supply coupling for coupling to said second water supply coupling, for passing the water stream through said auxiliary chamber from said water supply hose to said first water supply coupling.

2. A device according to claim 1, wherein said closure means comprises a sleeve moveable mounted to said water supply hose and removably connectable to said supply end of said handle housing, said auxiliary chamber opening extending through a side of said auxiliary chamber member and said sleeve having an interior sealing surface for sealing said auxiliary chamber opening.

3. A device according to claim 1, wherein said tool receiving rotor comprises an air operated turbine in said head end of said handle housing, an air supply line extending through said handle housing and communicating with said head end, said water supply means including a water supply line extending through said handle housing and connected to said first water coupling, an air supply hose extending along said water supply hose and air supply coupling means extending along said auxiliary chamber member for connecting said air supply hose to said air supply line.

4. A device according to claim 3 including an air return opening communicating said head end with an interior of said handle housing for returning air supplied by said air supply line through said handle housing, an air return hose extending along said water supply hose and air return coupling means extending along said auxiliary chamber member for connecting the interior of said handle housing to said air return hose.

5. A device according to claim 3, including an optical fiber bundle extending along said handle housing and terminating at the light emitting end adjacent said head end, a optical fiber hose extending along said water supply hose and light coupling means extending along said auxiliary chamber for coupling said optical fiber hose to said optical fiber bundle.

6. A handpiece device for use with a water stream and an additive comprising:
   a handle housing having a head end;
   a tool receiving rotor rotatably mounted to said head end for receiving a rotary tool to be used in a procedure;
   water supply means operatively connected to said handle housing for defining a water stream terminating at a water nozzle adjacent said head end;
   auxiliary chamber means connected to said handle housing and defining an auxiliary chamber communicating with said water stream, said auxiliary chamber including an opening for receiving an additive for introduction of the additive into the water stream; and
   closure means connected to said auxiliary chamber means for opening said auxiliary chamber opening to receive the additive and for closing the auxiliary chamber opening for sealing the auxiliary chamber against loss of water from said water stream;
   said auxiliary chamber being formed in said handle housing, said water supply means including a water line extending along said handle housing and terminating in said auxiliary chamber, and a screen in said auxiliary chamber for covering an opening of said water supply line into said auxiliary chamber, said auxiliary chamber opening extending through said handle housing and said closure means comprising a cap for closing said auxiliary chamber opening.

7. A device according to claim 6 including an air return opening communicating said head end with an interior of said handle housing, the interior of said handle housing comprising an air return channel extending around said auxiliary chamber.

8. A device according to claim 6 including an air return opening communicating said head end with an interior of said handle housing, an air return line extending in said handle housing, said auxiliary chamber being defined by a cage for confining additive, said water supply line comprising the interior of said handle housing.

* * * * *